United States Patent [19]
Farrar, Jr.

[11] 3,955,562
[45] May 11, 1976

[54] APPARATUS FOR MEASURING RANGE OF MOTION

[76] Inventor: Edward L. Farrar, Jr., 1315 S. Orange Ave., Orlando, Fla. 32806

[22] Filed: May 19, 1975

[21] Appl. No.: 578,549

[52] U.S. Cl. ................................................ 128/2 S
[51] Int. Cl.² ............................................ A61B 5/10
[58] Field of Search .................... 128/2 S, 2 R, 2.1; 340/279

[56] References Cited
UNITED STATES PATENTS

| | | | |
|---|---|---|---|
| 2,565,381 | 8/1951 | Leighton | 128/2 S |
| 3,258,007 | 6/1966 | Karpovich et al. | 128/2 S |
| 3,304,911 | 2/1967 | Hakata et al. | 128/2 S |
| 3,796,208 | 3/1974 | Bloice | 128/2 S |

*Primary Examiner*—Lawrence W. Trapp
*Attorney, Agent, or Firm*—Duckworth, Hobby & Allen

[57] ABSTRACT

The range of motion that an individual can move his head or other body portions can be measured and recorded in an apparatus having a base with a plurality of switches mounted thereto in a plurality of predetermined positions with each switch being actuated by movement of the base as the individual moves his particular body part through available angles in predetermined directions. The switches actuate a display board, having lights and/or a graph, to maintain a display of the available range of motion the individual can move his head or other body portion.

13 Claims, 7 Drawing Figures

APPARATUS FOR MEASURING RANGE OF MOTION

BACKGROUND OF THE INVENTION

The present invention relates to a device for measuring and recording the available ranges of motion of a portion of an individual.

In the field of orthopedic medicine, it is often necessary to measure the range of motion of different portions of the patient's body to determine disabilities and in diagnosing various diseases and injuries. The neck and lumbar regions are capable of a wide range of and motions and it is also desirable to measure and record motion of the upper or lower extremities of the body thereby providing a varied and otherwise difficult to describe range of body motions. A display would accordingly be advantageous to determine a more precise degree of disability utilizing measurements with sufficient accuracy to determine when improvement or regression have taken place. To combat the prior lack of accurate means of measuring, it has been suggested that various measuring and testing techniques be utilized to measure the range of motion of different portions of the human anatomy and these include attaching an angle measuring gauge with a strap to the head so that movement of the head parallel with the angle gauge will indicate the degree of angle that the head can be moved by the patient. This is somewhat inadequate inasmuch as it does not record the data and it measures only one angle rather than the full range of available motion and requires the moving of the gauge into a different position for measuring the angle and range of motion from each spot and hand recording the information.

The present invention on the other hand overcomes these limitations by allowing the patient to move a portion of his anatomy in any direction and move through various ranges of motions while the entire range of motion is recorded on a display board or graph for developing a precise chart of the movement capable of a particular patient. The present invention also provides for attaching to the head, chest, upper or lower extremities for making different measurements as desired by the physician.

SUMMARY OF THE INVENTION

An apparatus for measuring the various ranges of motion of a patient is provided in which a base has a plurality of switches mounted thereto and a plurality of predetermined positions, each switch being actuated by moving the base through a predetermined path to determine the angle in each direction of movement of the base. A hat, strap or other attaching member is connected to the base for attaching the base and switches to the head, chest or other body portion and a recording or display board is coupled to the plurality of switches for recording each actuated switch thereby generating a display or graph chart indicating the range of motion being measured for the patient.

BRIEF DESCRIPTION OF THE DRAWINGS

Other features and advantages of the present invention will be apparent from the written description and the drawings in which.

DESCRIPTION OF THE PREFERRED EMBODIMENT

Figure 1:
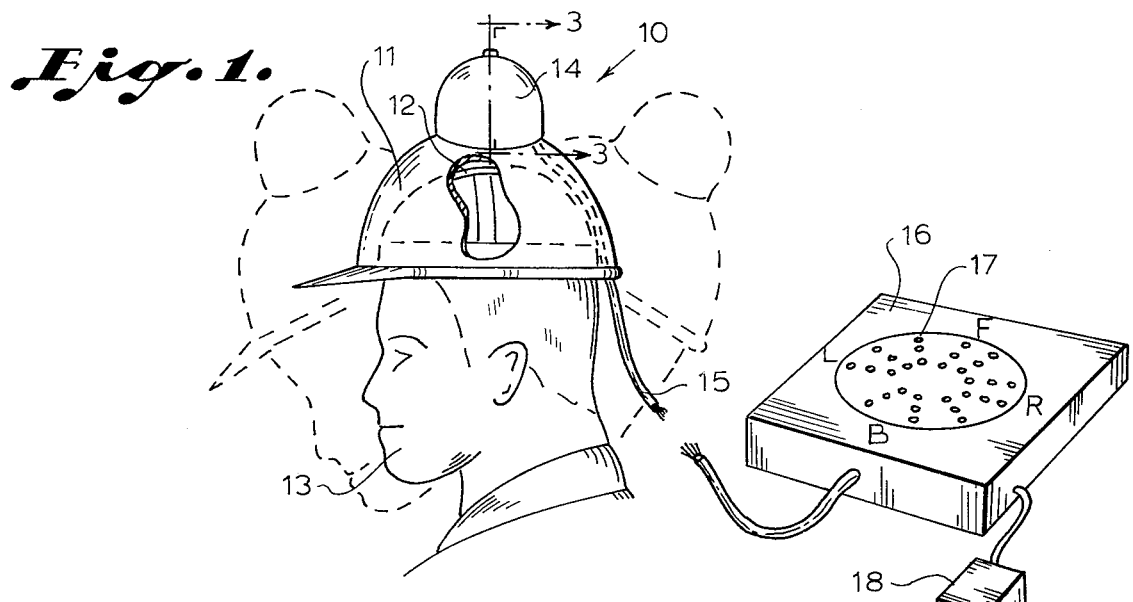
FIG. 1 illustrates a perspective view of a range of motion measuring apparatus in accordance with the present invention attached to a patient by means of a support pad and interconnected with a display board.
Figure 2:
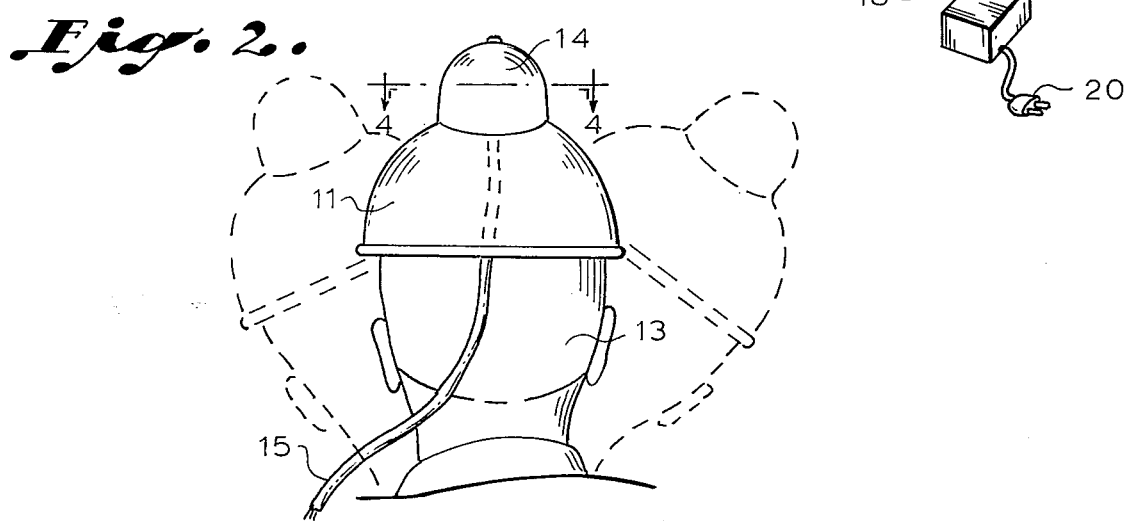
FIG. 2 is a rear elevation view of the apparatus in accordance with FIG. 1.

Referring now to FIGS. 1 through 5, a preferred embodiment of the present invention 10 is mounted to a hat support 11 having hat support straps 12 for attaching the hat to the head of a patient 13. The hat 11 has a casing 14 attached to the top thereof with a trunk line 15 having a plurality of electrical conductors therein running from the casing 14 out the back of the hat 11 to a display board 16. The display board has a plurality of lights 17 which may be electrical lights or light emitting diodes (LED), as desired, laid out in a generally x, y pattern for indicating the range of motion of the hat 11 and casing 12 on the patient 13's head. A power supply 18 is used to convert alternating current to a DC voltage and for lowering the voltage. A 110 volt alternating current electrical plug 20 is connected from the power supply 18 for connection to a power line. In general, movement of the patient's head with the hat mounted thereupon as illustrated in FIGS. 1 and 2 will light up predetermined lamps 17 on display board 16 and provide a chart of the range of motion the patient can move his head. A similar apparatus to the one in casing 14 can also be mounted to the chest or upper or lower extremities for measuring the range of motion of different portions of the patient's anatomy without departing from the spirit and scope of the invention.

Figure 3:
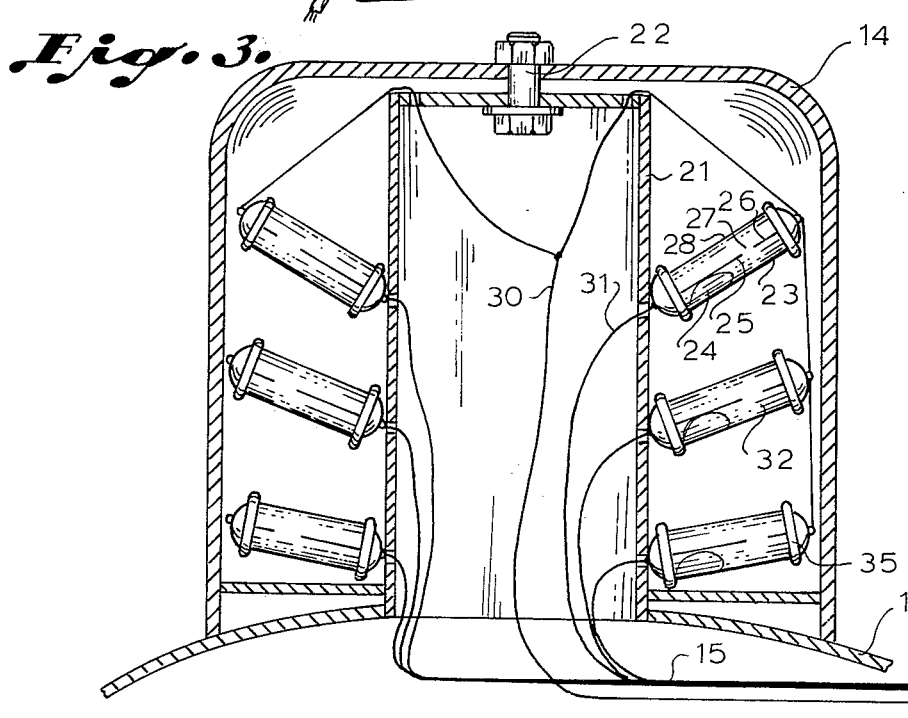
FIG. 3 is a sectional view taken along the line 3—3 of FIG. 1.
Figure 4:
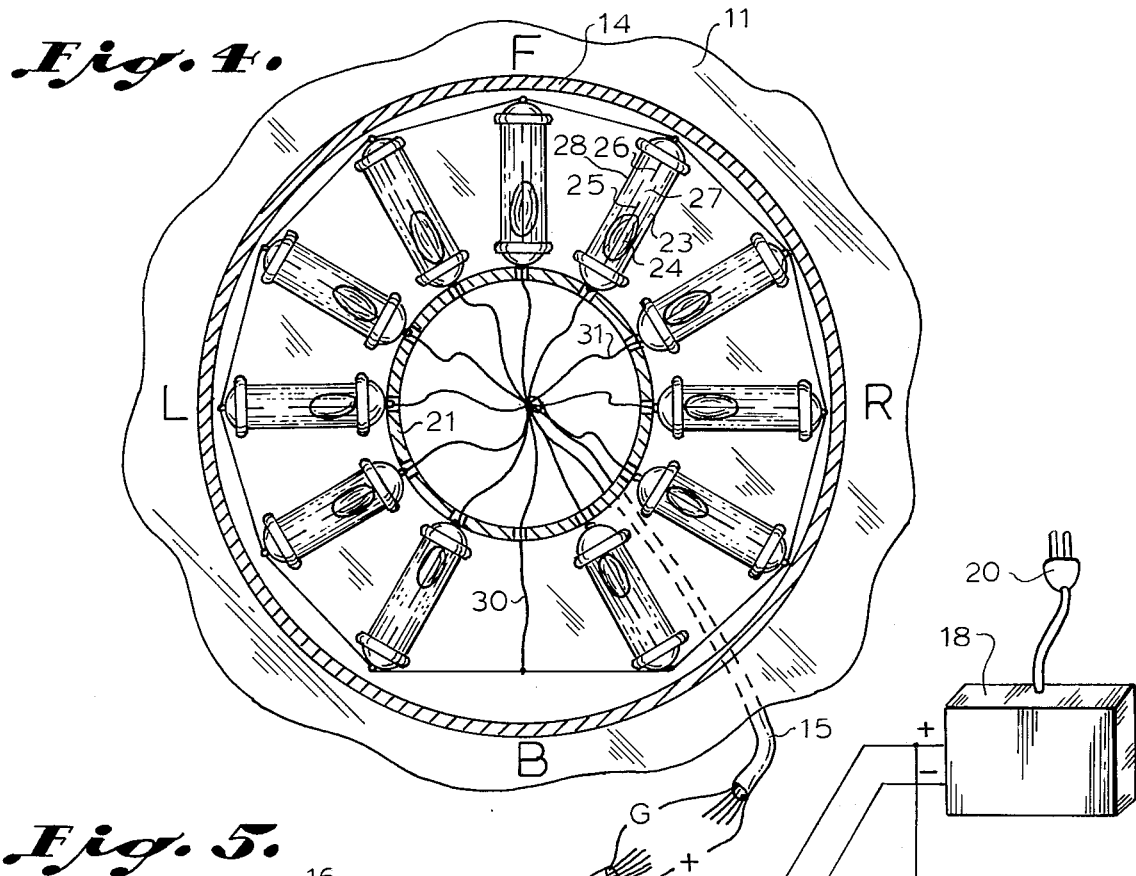
FIG. 4 is a sectional view taken along the line 4—4 of FIG. 2.
Figure 5:
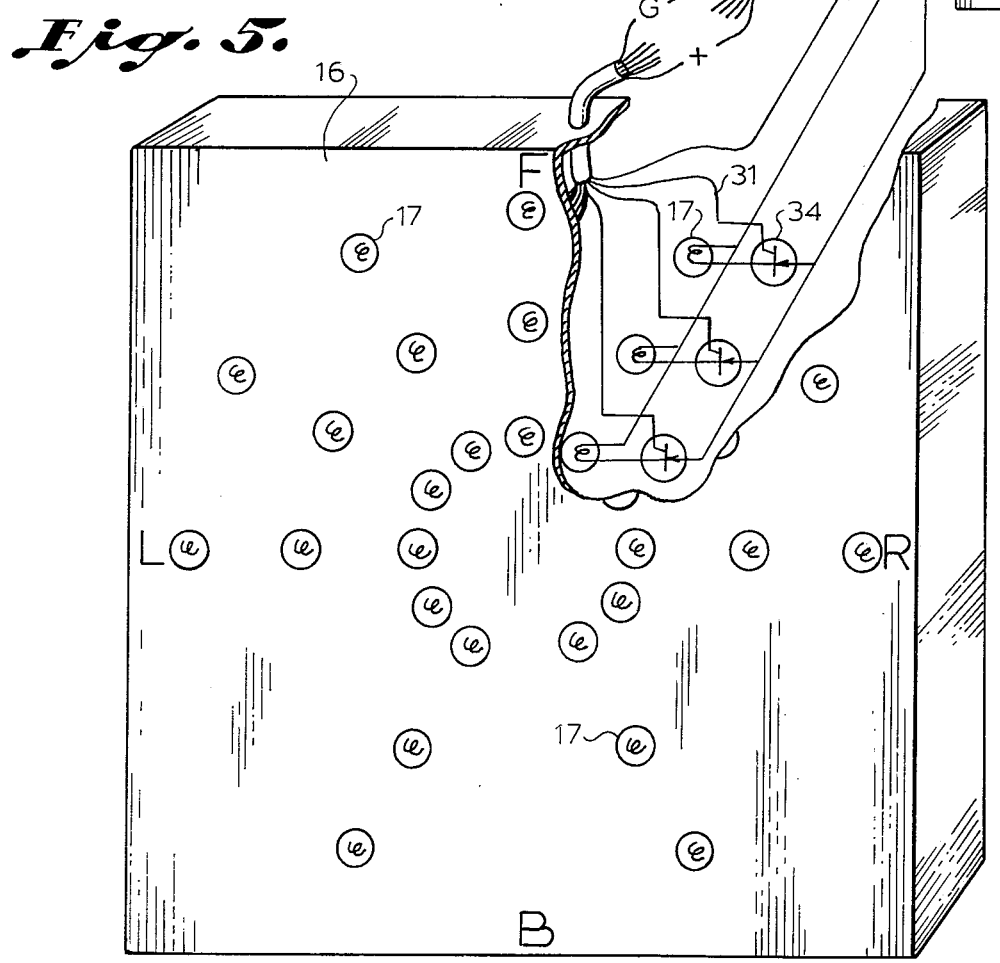
FIG. 5 is a cutaway, perspective view of a display board illustrating a plurality of display lights interconnected with switches and a power supply.

FIG. 3 illustrates that the casing 14 mounted to the hat 11 has a switch mounting base 21 mounted therein and attached to the casing 14 with a bolt 22. Switch mounting base 21 has a plurality of mercury switches 23 attached thereto at a set angle, each having a small amount of mercury 24 therein with a conductor 25 and a conductor 26 separated by a space 27 so that movement of the switch 23 so that the mercury 24 moves to one end thereof of a plastic or glass container 28 will close the contact between conductors 25 and 26 thereby allowing an electrical DC current to pass therethrough. A central ground 30 connects all of the switches 23 and each switch has an individual conductor 31 from the DC power source so that actuation of switch 23 allows the flow of current from the line 30 through the line 31 until the patient moves his head to move the mercury 24 away from the gap 27. The passing of current through the conductor 31 will actuate a predetermined lamp 17 on the display board 16 to show that the patient has been able to move through an angle sufficient to actuate a predetermined switch 23. To avoid the lamp 17 from going out when the head is moved through a further range of motion, a silicon controlled rectifier (SCR) or similar switch is actuated which holds the switch on until the entire apparatus is switched off. This allows the complete graph to be illustrated on the display board which can then be marked on graph paper, or alternatively, can be burned on heat sensitive graph paper placed over the display board 16 or by suitable photographic devices or by other means as desired. The plurality of switches 23 are mounted in spaced rows at different angles as illustrated in FIG. 3 with mercury switches 32 and 33 being mounted at different angles and in different positions so that each one takes a different angle of movement in the general direction of the switch in order to actuate the switch. A plurality of rows wrapped around the base 21 will thus provide a complete chart of the movement of the base 21 and the patient's head or other body portions. Each line 31, as well as grounding line 30, is fed through the trunk line 15 to the display board. As more clearly illustrated in FIGS. 4 and 5, eleven rows of three switches each are illustrated but depending upon the degree of accuracy necessary any number of switches can be utilized up to several hundred including additional rows of switches as well as additional switches within each row. FIG. 5 illustrates the SCR switches 34 connected to the lines 31 which in turn are connected to the lamps 17 which are illustrated as resistance lamps even though it should be clear that LED, or other light sources can be utilized without departing from the invention. The lamps produce heat and conveniently allow rapid charts to be recorded by the use of heat sensitive graph paper being placed over the front of the display 16.

Figure 6:
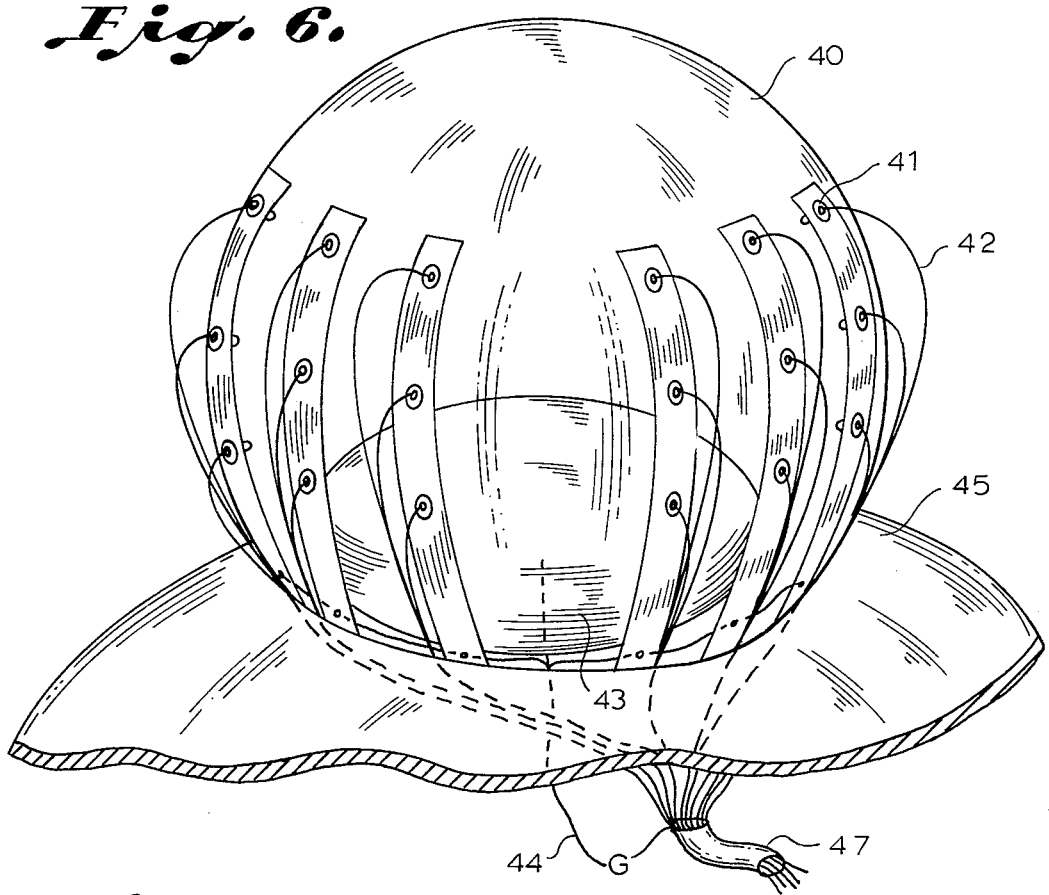
FIG. 6 is a perspective view of yet a second embodiment of the present invention.
Figure 7:
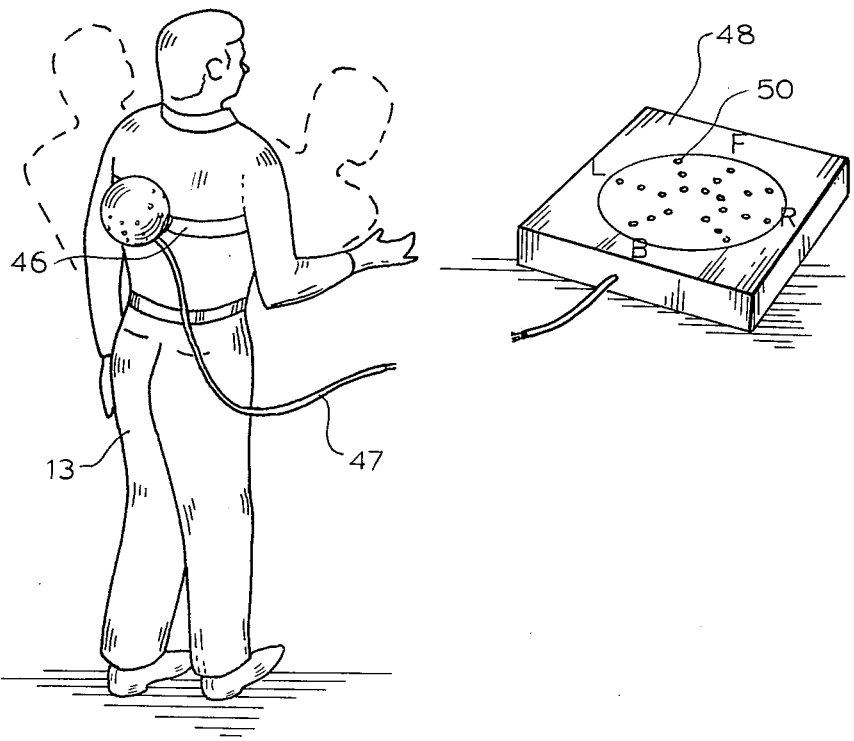
FIG. 7 illustrates a second body attached to a different portion of the patient.

If a large number of switches are to be utilized, it becomes cumbersome to assemble large numbers of individual switches and the embodiments illustrated in FIGS. 6 and 7 simplify this by having one large spherical container 40 having a plurality of probes or electrical contacts 41 each connected to an electrical conductor 42. The spherical container 40 is partially filled with mercury 43 which is connected to the crown by a ground wire 44. The spherical container is mounted to a base 45 which could be the hat 11 of FIGS. 1 and 2 or could be a mounting to a belt 46 as illustrated in FIG. 7. The plurality of lines 42 come off in a trunk linee 47 and are connected to the display board 48 having the plurality of lamps 50 thereon. Thus, rotation of the sphere 40 on the base 45 will allow the mercury 43 to shift in one direction making contact with the electrical contacts 41 thereby actuating or connecting a switch between the ground line 40 through the mercury 43 and the contact points 41 to complete a circuit actuating the lamp 50 which is maintained lit by SCR switches as previously described. The switching apparatus as llustrated in FIG. 6 can be utilized as illustrated in FIG. 7 connected to the chest for measuring the lumbar motion or to one of the upper or lower extremities of the patient 13 and can be made to be attached interchangably to different mounts for mounting to the different portions of the body by the physician.

When a large number of switches or contacts 41 are used with a large number of wires 42 low voltage trunk line can be used. These are commonly available for use in telephone and other circuitry with all of the lines having different color coded symbols which can be utilized for ease of manufacture of the apparatus. Switches, lamps, SCRs and power supplies are of course available for use in the present invention while a special switching sphere 40 would be required in this embodiment, it can be easily manufactured from glass, plastic or other materials with contacts or probes 41 protruding therethrough connected to wires on the exterior thereof for feeding into the trunk line 47. It should be clear at this point that movement in the various joints in the anatomy of a patient can be measured rapidly and the data recorded by a physician. It should, however, be clear that the present invention is not intended to be limited to the forms shown inasmuch as they are to be considered illustrative rather than restrictive.

I claim:

1. An apparatus for measuring the range of motion of an individual comprising in combination:
    a base;
    a plurality of switches mounted to said base in a plurality of predetermined positions, each switch being actuated by moving said base a predetermined angle in a predetermined direction;
    attaching means connected to said base for attaching said base and switches to an object to be tested; and
    recording means coupled to said plurality of switches for recording each actuated switch whereby a range of movement can be recorded on said recording means.

2. The apparatus in accordance with claim 1 in which said plurality of switches are each mercury switches.

3. The apparatus in accordance with claim 2 in which each switch is connected to a silicon controlled rectifier to maintain said recording means actuated.

4. The apparatus in accordance with claim 3 in which said attaching means includes a head mounting hat having said base and switches attached thereto.

5. The apparatus in accordance with claim 1 in which said attaching means is a belt having said base attached thereto for strapping said base to different portions of a patient.

6. The apparatus in accordance with claim 1 in which said plurality of switches have a plurality of contacts mounted to a container filled with a conductive liquid connected to one electrical source whereby movement of said conductive liquid will make contact with said contacts mounted thereon thereby closing a circuit with each contact.

7. The apparatus in accordance with claim 1 in which a plurality of wires connect each switch with a light source for actuating said light source on said recording means.

8. The apparatus in accordance with claim 1 in which said recording means includes a graph and graph marking means therein.

9. An apparatus for measuring the range of motion of an individual comprising in combination:
    a base;
    attaching means for attaching said base to a patient;
    a container mounted to said base, said container being partially filled with a conductive liquid;
    a plurality of first electrical contacts mounted through said container to predetermined points inside said container;
    a second electrical conductor connected to said container and electrically coupled to said conductive liquid whereby a current can flow between said second electrical conductor and said conductive liquid and between each of said plurality of first electrical contacts and said conductive liquid making contact therewith; and
    recording means connected to each of said plurality of contacts to record electrical current in said first conductive contacts whereby contact of each of said first contacts with said conductive fluid may be recorded.

10. An apparatus in accordance with claim 9 in which said conductive liquid is mercury.

11. An apparatus in accordance with claim 10 in which said recording means includes a plurality of light sources.

12. An apparatus in accordance with claim 11 including a plurality of switching means, one switching means connected to each first electrical contact and to each light source whereby current flowing through said first electrical contact will actuate a corresponding switching means and light source and will maintain said light source operative even when said conductive liquid contact is broken.

13. An apparatus in accordance with claim 12 in which said light sources are a plurality of light emitting diodes and said switching means includes a plurality of silicon controlled recitifier switches.

* * * * *